(12) United States Patent
Mennen

(10) Patent No.: US 6,254,840 B1
(45) Date of Patent: Jul. 3, 2001

(54) GAS-LIQUID CONTACTING APPARATUS

(75) Inventor: Johannes H. Mennen, Roggel (NL)

(73) Assignee: DSM N.V. (NL)

( * ) Notice: Subject to any disclaimer, the term of this patent is extended or adjusted under 35 U.S.C. 154(b) by 0 days.

(21) Appl. No.: 09/266,810

(22) Filed: Mar. 12, 1999

(30) Foreign Application Priority Data

Mar. 12, 1998 (NL) .................................................. 1008573

(51) Int. Cl.$^7$ ............................... B01J 8/04; B01J 10/00; F02M 29/04
(52) U.S. Cl. .......................... 422/195; 422/191; 422/193; 261/113; 261/114.1; 261/114.5
(58) Field of Search ................................... 422/193, 195, 422/191; 261/113, 114.1, 114.5

(56) References Cited

U.S. PATENT DOCUMENTS 3,779,525 * 12/1973 Tanigawa et al. ................. 261/114.1
3,864,439 * 2/1975 Tanigawa et al. ................. 261/114.1

FOREIGN PATENT DOCUMENTS

| 1 542 274 | 3/1970 | (DE) . |
| 95/31278 | 11/1995 | (WO) . |
| 98/03477 | 1/1998 | (WO) . |

OTHER PUBLICATIONS

Patent Abstracts of Japan vol. 2, No. 100 (C–020) Aug. 18, 1978 & JP 53 062784 A (Kobe Steel Ltd.), Jun. 5, 1978 zie samenvatting; figuren & Database WPI Section Ch, Week 7828 Derwent Publications Ltd., London, GB; Class J04, AN 78–50574 XP002085692 & JP 53 062784 (Kobe Steel Ltd.) zie samenvatting.
Patent Abstracts of Japan vol. 10, No. 185 (C–357) Jun. 27, 1986 & JP 61 035845 A (Mitsubishi Heavy Ind. Ltd.), Feb. 20, 1986 zie samenvatting; figuren & Database WPI Section Ch, Week 8614 Derwent Publications Ltd., Londaon, GB; Class J04, AN 86–090613 XP002085693 & JP 61 035845 A (Mitsubishi Heavy Ind. Co. Ltd.), Feb. 20, 1986 zie samenvatting.

* cited by examiner

*Primary Examiner*—Hien Tran
*Assistant Examiner*—Alexa A. Doroshenk
(74) *Attorney, Agent, or Firm*—Pillsbury Winthrop LLP

(57) ABSTRACT

An apparatus for effecting gas-liquid contact in a system in which the liquid is the continuous phase, the apparatus consisting of a vertical column fitted with a series of perforated trays. The perforated trays provide openings near the edges of the trays or between the trays and the inside of the column wall for the transport of liquid. The trays also include a downwardfacing flange at or near the tray edge to establish and maintain a gas cushion under the tray, the height of the flange being between 5–50% of the tray-to-tray spacing The trays further including an upwardly-facing rim on the top side of the tray within which are provided perforations designed for gas flow, the height of the rim being between 5–50% of the tray-to-tray spacing. Between adjacent trays is provided a generally cylindrical tube having a diameter smaller than that of the downwards-facing flange and larger than the upwards-facing rim, the height of the cylinder being 40–80% of the distance between two successive trays.

14 Claims, 4 Drawing Sheets

GAS-LIQUID CONTACTING APPARATUS

The invention relates to an apparatus for effecting gas/liquid contact in which the liquid forms the continuous phase. In particular; the invention relates to a reactor for preparing urea from ammonia and carbon dioxide. The invention also relates to an apparatus for the hydrolysis of urea in aqueous solutions.

Gas/liquid contact in which the liquid forms the continuous phase can be achieved in liquid-filled columns also known as bubble columns or bubble-type washers. Bubble columns may be configured in a variety of ways and may include random or structured packing materials and are often used as strippers or reactors. As described in US-A-3046307, a vertical bubble column may be is divided into a number of compartments by a series of perforated baffles, plates, or trays positioned horizontally across the column.

In bubble columns the gas phase and the liquid phase are ideally in constant intensive contact with one another throughout the entire column volume. In those bubble columns utilizing perforated trays, the gas and liquid phases are redistributed as they pass through the perforations. Although countercurrent flow may be more common, the gas phase and the liquid phase can also be passed through appropriately configured bubble columns as cocurrent or crosscurrent flows. Bubble column can be particularly useful for synthesizing urea from ammonia and carbon dioxide and for hydrolyzing urea in aqueous solutions.

A variety of bubble column configurations are possible, but common commercial designs include vertical columns about 1 to 5 meters in diameter with column heights of about 5 to 40 meters. Bubble columns used to synthesize urea from ammonia and carbon dioxide preferably have a diameter of between 1.5 and 4 meters and a height of between 10 and 35 meters.

Columns for promoting gas/liquid contact in systems in which liquid is the continuous phase are frequently provided with structures that divide the column into a plurality of compartments. To achieve this result, a column may be fitted with structured packings, trays, or a combination of structures, that define separate compartments within the column. Each of the compartments can be considered as a "continuously stirred tank reactor" (CSTR) in which the turbulent flow of the gas and/or liquid phases produces the desired stirring. In the following discussion of the present invention, reference will be made to CSTRs and compartments to describe a preferred embodiment of the present invention but such terms should be understood as descriptive rather than limiting.

The number of compartments provided in such a column is usually at least two, preferably at least five, and less than 40, preferably less than 20. The compartments are preferably formed by inserting a series of horizontal trays across the column.

If a slow reaction takes place in the liquid phase, the degree of conversion in the liquid phase can be substantially increased if the liquid phase is passed through the installation as a so-called plug flow. The contact between the gas phase and the liquid phase may result in the condensation of part of the gas phase. For example, during the preparation of urea, the heat of condensation is used for dehydrating the ammonium carbamate to form urea.

To realize a high degree of conversion, a column suitable for synthesizing urea is usually divided into a plurality of compartments lying one above the other defined by a series of horizontal trays spaced generally evenly along the length of the column as described in US-A-3046307. In this way the synthesis column is divided into a number of compartments arranged in the flow direction of the reaction mixture with the intention of providing uniform mixing of the reaction components in each of the compartments. The horizontal trays according to US-A-3046307 extend across the full width of the column and are fitted with a multitude of openings for the passage of the two-phase gas/liquid stream. However, in a column according to US-A-3046307, as gas and liquid flow through the same openings, areas of reduced flow are created that form stagnant zones within the column where no, or virtually no, flow occurs. The presence of these stagnant zones reduces the overall conversion of the reagents and degrades the column efficiency.

An alternative construction for a tray column provides for generally annular openings between the horizontal trays and the inside wall of the column. If the trays are also perforated, the fluid phase can flow through the annular openings while the gaseous phase can flow through the tray perforations. In such a configuration, however, there is a risk that the liquid phase will flow along the wall without making sufficient contact with the gas phase. This phenomenon is referred to as 'bypassing' and may reduce the degree of conversion achieved by the column.

Another phenomenon that has been identified as producing a reduced degree of conversion is referred to as 'backmixing.' Backmixing when a portion of the liquid phase flows in a direction opposite that of the intended direction of flow, for example via the perforations, as is described in US-A-4098579. In the case of 'backmixing,' the failure to maintain the optimum plug flow through the reactor degrades the reactor performance and reduces the yield.

An objective of the present invention is an improved apparatus for achieving improved gas/liquid contact in a system in which the liquid is the continuous phase to achieve a degree of conversion approximating the theoretically possible value.

In particular, the invention's objective is an improved reactor design suitable for preparing urea from ammonia and carbon dioxide and for the hydrolysis of urea in aqueous solutions.

A further objective of the invention is to provide trays that prevent backmixing, bypassing, and stagnant zone behavior. In particular, a further objective of the invention is a reactor design that improves the urea yield of the urea reaction and increases the throughput of the reaction components.

A further objective of the invention is to provide method suitable for coverting and modernizing existing vertical columns for both synthesis and stripping operations, particularly in urea plants. Yet a further objective of the invention is to provide a method suitable for modernizing vertically arranged hydrolyzer to decrease the effluent urea content while maintaining throughput and/or increase the reactor throughput without increasing the effluent urea content.

These objectives can be realized with an apparatus consisting of a vertical column fitted with perforated trays having an opening near the edge of the tray or between the tray and the inside column wall for liquid flow, a generally circular flange along the lower edge of the tray to create a gas cushion under the tray, a generally circular rim on the top side of the tray containing the perforations for gas flow, and a cylinder positioned between two adjacent trays that has a diameter smaller than the downward flange and larger than the diameter of the circular rim, the height of the cylinder being 40–80% of the distance between the two trays.

Figure 1:
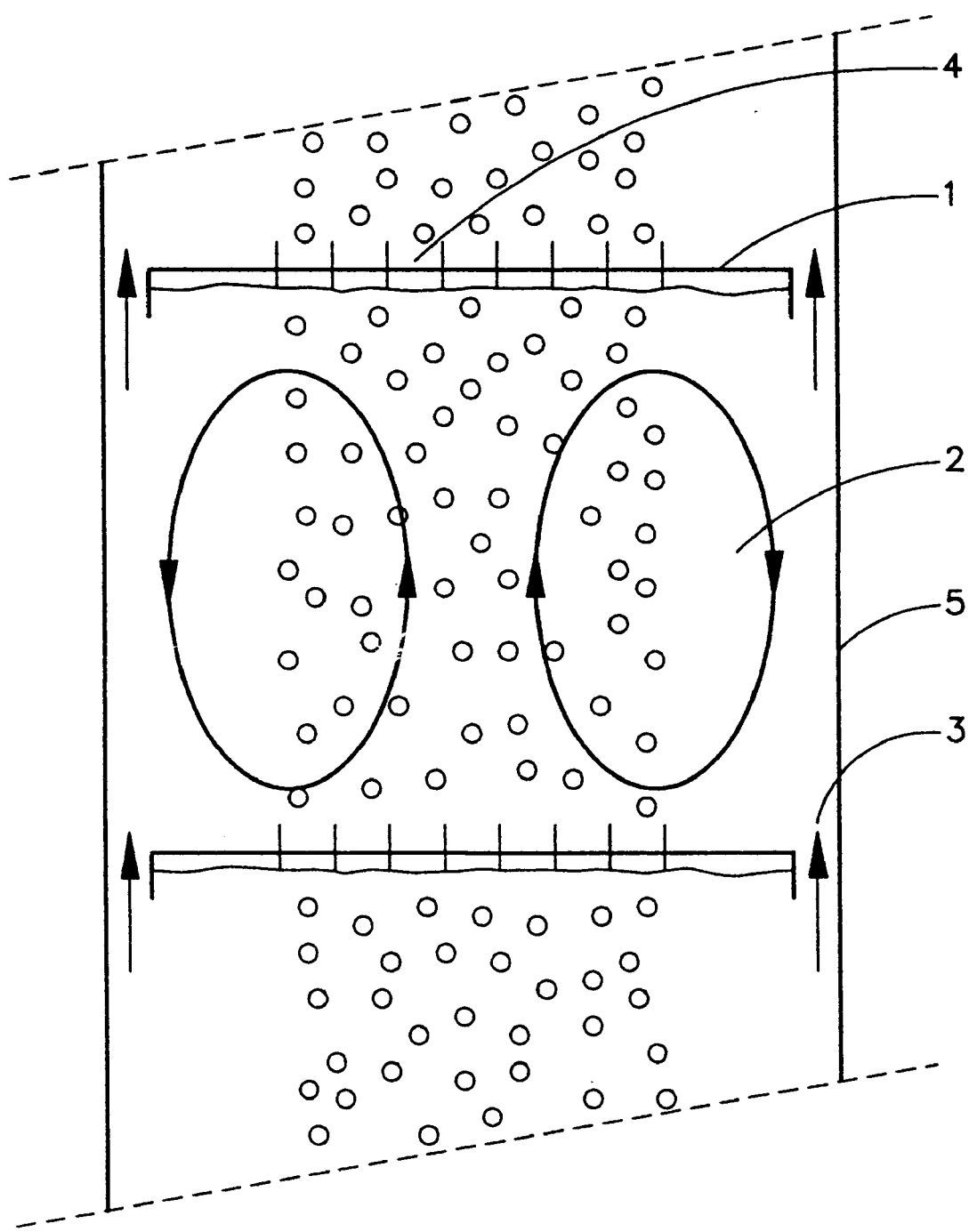
FIG. 1 illustrates a portion of a gas/liquid reactor according to the prior art.

In practice, urea reactors are often designed with between seven and 12 trays and, in particular, 10 or 11 trays. Urea reactors commonly include a small annular opening (1 to 2 mm) between the trays and the reactor wall to prevent corrosion. Although a portion of the liquid flow occurs through these annular openings, the bulk of the liquid flow occurs through special holes or perforations made in the trays, preferably at or near the edge of the trays. The liquid holes may be positioned differently on adjoining trays to create a zigzag liquid flow through the column.

According to the invention; the height of the downwards-facing flange at the edge of the tray can be 50–2000 mm, preferably 100–1000 mm, and should comprise less than ½, and preferably less than ¼, of the distance between two trays. In particular, the height of the downwards-facing flange is 5–50% of the distance between two adjacent trays. The diameter of the downwards-facing flange will approximate that of the tray itself.

Similarly, the height of the rim on the top side of the tray is 10–2000 mm, preferably 50–1000 mm, and should comprise less than ½, and preferably less than ¼, of the distance between two trays. In particular, the height of the upwards-facing rim is 5–50% of the distance between two adjacent trays. Further, the diameter of the rim on the top side of the tray should be less than 95%, preferably between 40 and 80%, and most preferably between 50 and 70%, of the diameter of the tray itself.

The height of the cylinder positioned between two adjacent trays is 50–4000 mm and is preferably less than ¾ of the distance between the trays The diameter of the cylinder should be larger than the diameter of the upwards-facing rim and should be less than 95%, preferably between 40 and 80%, and most preferably between 50 and 70%, of the diameter of the tray itself.

According to the invention, the gas stream is fed into a compartment via the gas perforations positioned within the circular rim on the top side of the tray. Feeding the gas stream in this manner creates a density difference between the two-phase stream inside the cylinder and the portion of the liquid stream between the cylinder and the inner wall of the column. This density difference creates siphonage, drawing liquid into the cylinder and increasing the mixing achieved within the compartment. The mixing is further improved by utilizing the rim on the top side of the tray and the cylinder to produce a venturi effect, thereby drawing additional liquid into the cylinder. These effects increase the circulation ratio and achieve a higher degree of mixing within such a compartment. A number of such CSTRs arranged in series approximates an ideal plug flow within a reactor.

Although the distance between two trays may vary widely, typically between 500 and 5000 mm, but they are generally installed in a column with nearly equal spacing distances and preferably oriented almost parallel to one another.

According to the present invention, the openings provided for the liquid stream should provide for a liquid flow rate of between 0.05 and 1 m/sec, preferably between 0.10 and 0.60 m/sec, and most preferably, between 0.10 and 0.30 m/sec. For example, in a urea reactor, it is contemplated that the openings provided for the liquid stream should comprise between 1 and 10% of the cross-section of the reactor to achieve the desired flow rates. The openings provided for the liquid stream may be of any shape, for example an annulus along the wall, a square, round or elliptical openings, or part of a circle segment, etc.

According to the present invention, a gas flow rate through the openings provided of at least 2.5 m/sec is advantageous. It is contemplated that acceptable gas flow rates may be between 2.5 and 20 m/sec, and more preferably between 2.5 and 10 m/sec. Maintaining the desired gas flow rates both prevents backmixing and increases the degree of conversion achieved within the reactor to a value approximating the theoretical conversion value. The number, size and distribution of the perforations can be varied between the various trays. For circular perforations, it is contemplated that the minimum size would be about 2 mm, preferably between 2–20 mm, and more preferably between 3 and 10 mm. The perforations may also have a square or elliptical shape or the shape of part of a circle segment.

The installation according to the invention is particularly suitable for carrying out a process for the preparation of urea at a temperature below 250° C., preferably between 160 and 200° C. The pressure is then below 25 MPa, preferably between 12 and 20 MPa and in particular between 12 and 17.5 MPa.

The invention is generally suitable for use in reactors carrying out processes in which a slow chemical reaction takes place in the liquid phase. In particular, the invention is suitable for use in reactors carrying out processes in which ammonium carbamate is converted into urea or in which urea is hydrolysed to form ammonium carbamate.

The present invention is also particularly suitable for modernizing existing urea plants by providing an improved structure for replacing the conventional trays or packing in existing reactors or strippers, thereby providing substantial performance improvements.

Urea can be prepared by introducing ammonia and carbon dioxide into a synthesis zone at a suitable pressure (for example 12–40 MPa) and a suitable temperature (for example 160–250° C.), which first leads to the formation of ammonium carbamate according to the reaction:

$$2NH_3 + CO_2 H_2N\text{—}CO\text{—}ONH_4$$

Dehydration of the ammonium carbamate formed then leads to urea according to the equilibrium reaction:

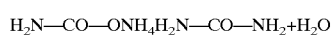

$$H_2N\text{—}CO\text{—}ONH_4 H_2N\text{—}CO\text{—}NH_2 + H_2O$$

The degree to which this last conversion takes place is dependent on, for example, the temperature and the amount of excess ammonia used. The reaction product obtained from the reaction is a solution consisting substantially of urea, water, ammonium carbamate, and unbound ammonia. The ammonium carbamate and the ammonia must then be removed from the solution and preferably recycled to the synthesis zone. In addition to the liquid reaction product, a gas mixture comprising ammonia, carbon dioxide, and inert gases is formed in the synthesis zone. Ammonia and carbon dioxide are removed from this gas mixture and are preferably recycled to the synthesis zone. The synthesis zone may consist of separate zones for the formation of ammonium carbamate and urea. These zones may however also be united in a single apparatus.

The theoretically realizable degree of conversion of ammonia and carbon dioxide into urea is determined by the thermodynamic position of the equilibrium and depends on for example the $NH_3/CO_2$ ratio, the $H_2O/CO_2$ ratio and the temperature. Knowing the reaction conditions, the theoretical degree of conversion be calculated with the aid of equilibrium models such as those described in Bull. of the Chem. Soc. of Japan 1972, Vol. 45, pp. 1339–1345, and J. Applied Chem. of the USSR (1981), Vol. 54, pp. 1898–1901.

The conversion of ammonium carbamate into urea and water in the synthesis zone can be improved by ensuring a sufficiently long residence time of the reaction mixture in the synthesis zone. The residence time will generally be more than 10 minutes, preferably more than 20 minutes, and generally less than 2 hours, preferably less than 1 hour. Preferably the residence time of the urea synthesis solution in the synthesis zone is chosen so that at least 90%, and more preferably, at least 95%, of the theoretically realizable amount of urea is obtained. At a higher temperatures and pressures, shorter resident times in the synthesis zone are often sufficient for obtaining a high degree of conversion.

In practice, a variety of different processes have been used for the commercial preparation of urea. Prior to 1970, urea was commonly prepared in so-called conventional high-pressure urea plants. Toward the end of the 1960s, however, these high-pressure plants were succeeded by processes carried out in so-called urea stripping plants.

As used herein, 'conventional high-pressure urea plant' should be understood to refer to a urea plant in which the decomposition of the ammonium carbamate not converted into urea and the expulsion of the usual excess amount of ammonia take place at a pressure that is substantially lower than the pressure in the synthesis zone itself. The synthesis zone in a conventional high-pressure urea plant usually operated at a temperature of 180–250° C. and a pressure of 15–40 MPa. The unconverted reagents from a conventional high-pressure urea plant, preferably operating according to the conventional recycle process, after expansion, dissociation and condensation, are recycled as a carbamate stream to the urea synthesis at a pressure of between 1.5 and 10 MPa. In a conventional high-pressure urea plant ammonia and carbon dioxide are moreover fed directly to the urea reactor. The molar $NH_3/CO_2$ ratio (N/C ratio) in the urea synthesis in a conventional high-pressure urea process is generally between 3 and 5.

These conventional urea plants were initially designed as so-called 'Once-Through' processes. In these processes, the non-converted ammonia was neutralized with acid (for example nitric acid) and converted into ammonium salts (for example ammonium nitrate). The great disadvantage of this process was this large amount of ammonium salt and the low degree of $CO_2$ conversion. These conventional 'Once-Through' urea processes were soon replaced by the so-called Conventional Recycle Processes, in which the majority of the non-converted ammonia and carbon dioxide are recycled to the synthesis zone. This recycling is generally effected in two steps utilizing a first recycling step at intermediate pressure (1.4–10 MPa) and a second recycling step at low pressure (0.1–0.6 MPa). In the first recycling step the urea synthesis solution coming from the reactor is heated to decompose the ammonium carbamate into gaseous ammonia and carbon dioxide and to evaporate the excess ammonia. This gas mixture is then converted into pure ammonia and an aqueous ammonium carbamate stream in a rectifying column. The two streams are then recycled to the urea synthesis. In the second recycling step the urea solution is again heated and subsequently separated. The resulting gas stream is condensed and subsequently fed to the rectifying column of the first step. The urea solution is then evaporated at reduced pressure to remove the water to produce urea. The two recycling steps and the evaporation together constitute the main part of the upgraded urea process. Variants of these conventional processes are also known, in which use is made of three recycling steps; the first recycling step is then operated at a pressure level of 2.5–12 MPa; the next ones at 1.2–3 MPa and 0.1–0.6 Mpa, respectively.

As used herein, a 'urea stripping plant' should be understood to refer to a urea plant in which the decomposition of the uncoverted ammonium carbamate and the separation of the usual excess ammonia takes place at a pressure that is essentially the same as the pressure in the synthesis zone. This decomposition/separation takes place in a stripper, with or without with the addition of a stripping medium. Carbon dioxide and/or ammonia can be used as the stripping gas in a stripping process before feeding these components into the synthesis reactor: The stripping occurs in a stripper positioned downstream from the synthesis reactor, in which the urea synthesis solution, typically containing urea, ammonium carbamate, water, ammonia, and carbon dioxide, is stripped while heat is supplied. It is also possible to use thermal stripping here. Thermal stripping means that ammonium carbamate is decomposed exclusively by heating the solution and the ammonia and carbon dioxide present are removed from the urea solution. Process variants are known in which this stripping takes place in two or more steps; in each of these stripping steps a stripping medium may or may not be supplied. The gas stream containing ammonia and carbon dioxide withdrawn from the stripper is preferably recycled to the synthesis via a high-pressure carbamate condenser.

The gas mixture formed during the urea synthesis may be removed from the synthesis section via a purge stream. In addition to the condensable ammonia and carbon dioxide, this gas mixture (synthesis off-gas) also contains inert gases such as nitrogen, oxygen and, possibly, hydrogen. These inert gases, which originate from the raw materials and from the make-up air in the carbon dioxide feed, protect the reactor materials against corrosion. This gas stream is typically discharged from the synthesis section after the reactor or after the high-pressure carbamate condensation, depending on the process route chosen. For example, the condensable components (ammonia and carbon dioxide) can be absorbed in a high-pressure scrubber operating at or near synthesis pressure before the inert gases are blown down. In such a high-pressure scrubber the condensable components, ammonia and carbon dioxide, may be subsequently absorbed from the synthesis off-gas into the low-pressure carbamate stream provided by additional equipment upgrades. This washing process in the high-pressure scrubber can be enhanced with a heat exchanger that extracts heat from the process. It is also possible during the removal of the greater part of the condensable components from the off-gas by extracting heat from the off-gas exclusively by means of a heat exchanger and without using the carbamate stream as an absorption agent. The carbamate stream from the high-pressure scrubber containing the ammonia and carbon dioxide absorbed from the synthesis off-gas is optionally recycled to the synthesis reactor via the high-pressure carbamate condenser. The synthesis reactor, high-pressure scrubber, stripper, and high-pressure carbamate condenser are the most important components of the high-pressure part of a urea stripping plant.

The synthesis reactor in a urea stripping plant is preferably operated at a temperature of 160–250° C., and more preferably at a temperature of 170–200° C. The pressure in the synthesis reactor is typically 12–25 MPa and preferably 12.5–17.5 MPa. The N/C ratio in the synthesis in a stripping plant is typically between 2.5 and 5. The synthesis can be carried out in one or more reactors. For example, if two reactors are used, the first reactor can be operated using fresh raw materials and the second using a proportion of raw materials recycled from other components or parts of the plant.

An embodiment often used for preparing urea is the Stamicarbon $CO_2$-stripping process as described in European Chemical News, Urea Supplement of Jan. 17, 1969, pp. 17–20. The urea synthesis solution formed in the synthesis zone at a high pressure and temperature is subjected to a stripping treatment at the synthesis pressure by bringing the solution into countercurrent contact with gaseous carbon dioxide and supplying heat. The greater part of the ammonium carbamate present in the solution is decomposed into ammonia and carbon dioxide with the decomposition products being expelled from the solution as gases and discharged together with a small amount of water vapor and the carbon dioxide added for stripping the solution. In addition to the carbon dioxide enhanced stripping described in this publication, effective stripping treatments can also be carried out thermally, using gaseous ammonia as a stripping gas, or using a mixture of the aforementioned gases. The greater part of the gas mixture obtained in the stripping treatment is condensed and adsorbed in a high-pressure carbamate condenser, after which the ammonium carbamate is recycled to the synthesis zone for the formation of urea.

The high-pressure carbamate condenser can for example be designed as a so-called submerged condenser as described in NL-A-8400839. The gas mixture to be condensed is then fed into the shell of a shell-and-tube heat exchanger with a diluted carbamate solution coming from the high-pressure scrubber. The heat of dissolution and condensation consequently released is discharged with the aid of a medium flowing through tubes, for example water, which is in the process converted into low-pressure steam. The submerged condenser can be arranged horizontally or vertically. It is however particularly advantageous to carry out the condensation in a horizontally arranged submerged condenser (a so-called pool condenser; see for example Nitrogen No. 222, July–August 1996, pp. 29–31), because, in comparison with a vertically arranged submerged condenser, the liquid usually has a greater residence time in the horizontally arranged condenser. This results in the formation of extra urea, which raises the boiling point, so that the difference in temperature between the urea-containing carbamate solution and the cooling medium increases, resulting in better heat transfer.

After the stripping treatment, the pressure of the stripped urea synthesis solution in the urea-upgrading section is reduced and the solution is evaporated, to obtain urea. This urea upgrading is carried out in one or more pressure steps, depending on the extent to which carbamate has already been removed in the stripper(s). The upgrading results in a low-pressure carbamate stream. This low-pressure carbamate stream is recycled to the section operating at synthesis pressure, for example via the high-pressure scrubber. In the high-pressure scrubber this low-pressure carbamate stream removes the bulk of the non-converted ammonia and carbon dioxide from the gas mixture blown down from the section operating at synthesis pressure for the purpose of removing the non-condensable gases from the synthesis section.

The upgrading also results in the formation of a water stream which contains traces of urea and ammonia and which must be purified. This purification can be accomplished with a two-step process in which the water stream is first stripped with steam or another gas and then held at high temperature for sufficiently long residence time to hydrolyze the remaining urea. The first and second steps can be carried out in a single apparatus or separately. It is advantageous to design the part of the water purification section in which the hydrolysis takes place as a bubble column according to the present invention. The plug-flow performance achieved by the present invention ensures that the column volume is more completely exploited and provides a degree of liquid/gas contact to maintain better temperature uniformity throughout the reactor.

The temperature during the hydrolysis step is usually between 150 and 300° C., preferably between 160 and 260° C. The pressure is then between 0.5 and 3 MPa, preferably between 1.2 and 2.4 MPa. During the hydrolysis step in a urea plant the amount of steam consumed is between 10 and 100 kg of steam, preferably between 20 and 60 kg of steam, per ton of urea produced.

The invention will be further elucidated with reference to the following FIGS. 1–4. FIG. 1 shows part of a urea reactor according to the state of the art. It contains perforated trays (1) for the transport of gas (4) which form compartments (2) having virtually the same volume as the compartments lying above and below. Liquid transport takes place in the annular space (3) between the perforated trays and the reactor wall (5).

Figure 2:
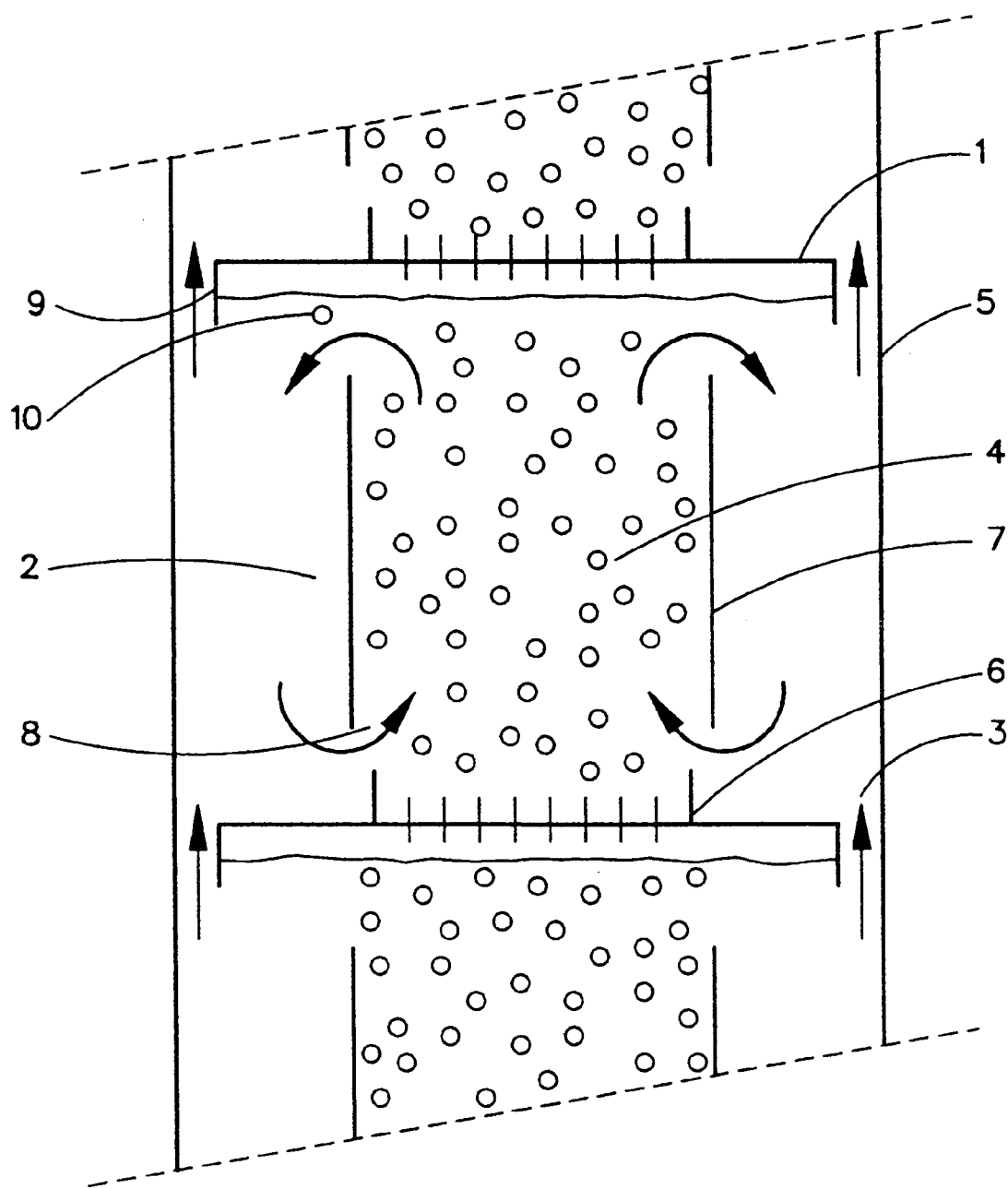
FIG. 2 illustrates a portion of a gas/liquid reactor according to the present invention.

FIG. 2 shows part of a urea reactor according to the invention containing perforated reactor trays (1) which form compartments (2) having virtually the same volume between two adjacent reactor trays and the inside of the reactor (5). Liquid transport takes place in the annular space between the perforated tray and the reactor wall (5). The gas phase is transported in the central part (4) of the perforated tray. The upright rim (6) and the cylinder (7) together torm the narrow passage (8) for sucking up the liquid phase for contact with the gas phase. The downwards-facing flange (9) and the cylinder (7) together form the contracted passage (10) for the returning liquid stream.

Figure 3:
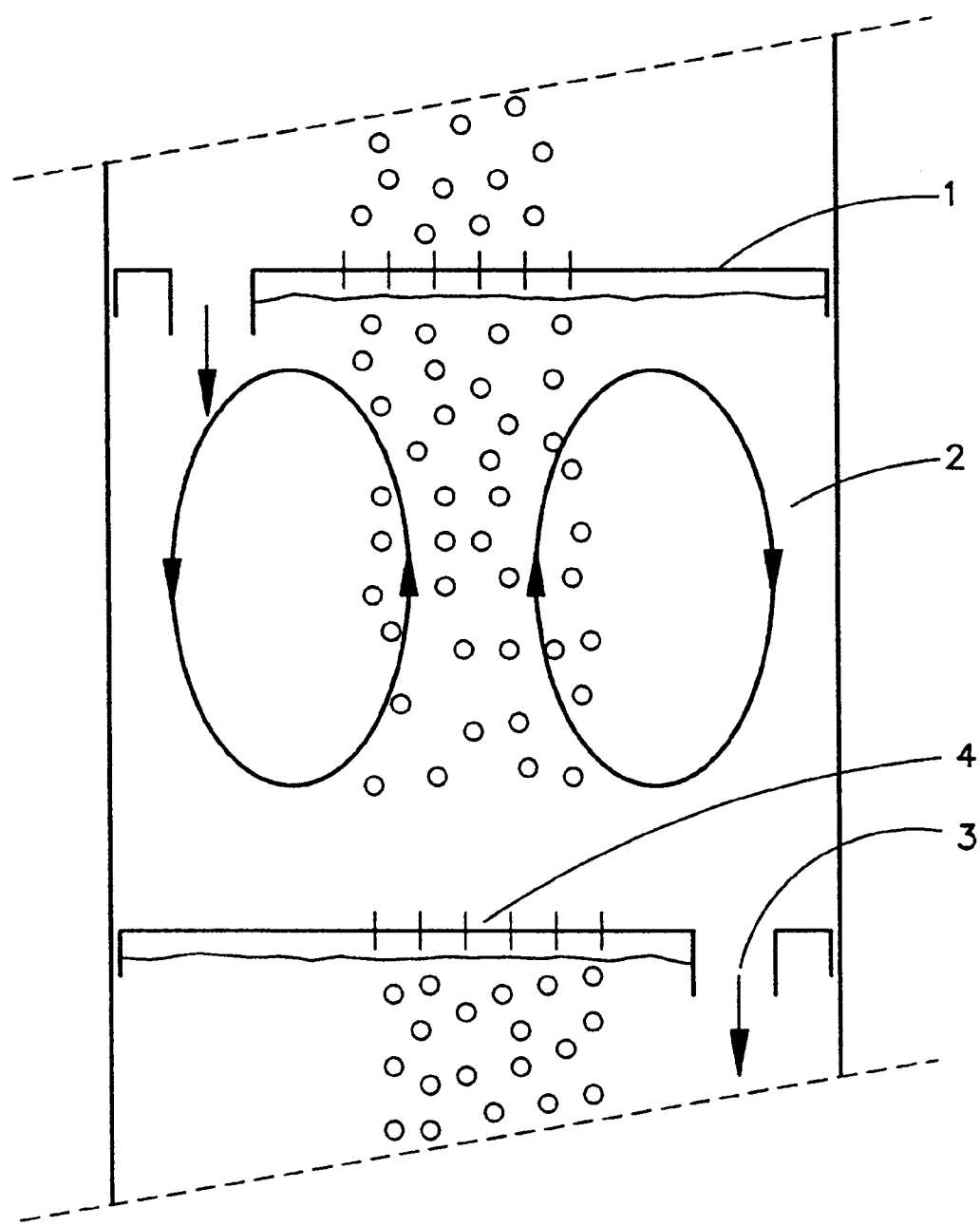
FIG. 3 illustrates a portion of a hydrolyzer according to the prior art.

FIG. 3 shows part of a hydrolyzer according to the state of the art. The perforated trays (1) form compartments (2) having virtually the same volume between two adjacent trays and the inside of the hydrolyzer. Liquid transport takes place in the downcomers (3). The gas (steam) is transported in the central part (4) of the perforated tray.

Figure 4:
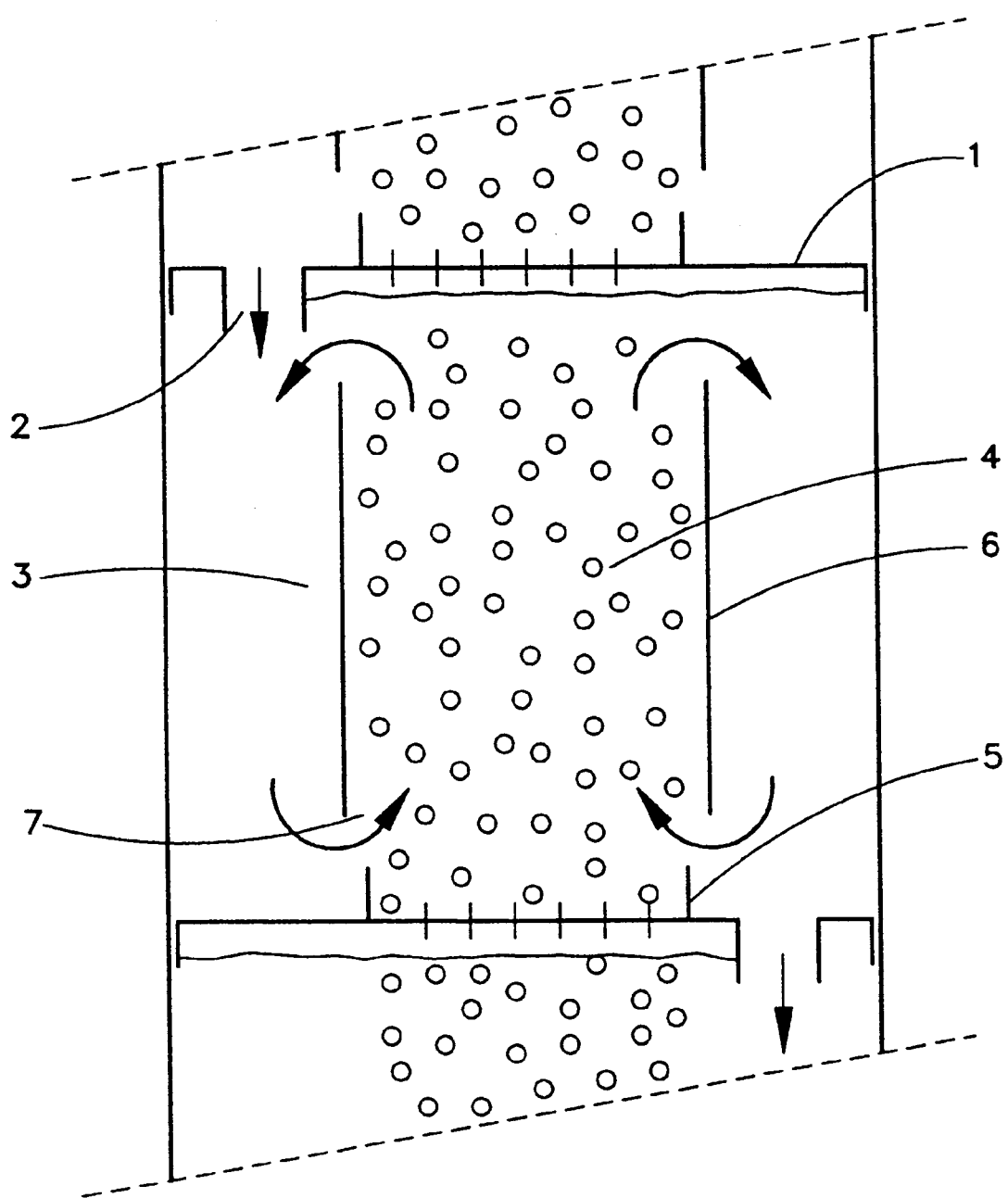
FIG. 4 illustrates a portion of a hydrolyzer according to the present invention.

FIG. 4 shows part of a hydrolyzer according to the invention. It contains perforated hydrolyser trays (1) and liquid downcomers (2). The perforated hydrolyzer trays form compartments (3) having virtually the same volume between two adjacent hydrolyzer trays and the inside of the hydrolyzer. Liquid transport takes place in the liquid downcomers (2). The gas phase (steam) is transported in the central part (4) of the perforated tray. The upright rim (5) and the cylinder (6) together form the narrow passage (7) for sucking up the liquid phase for contact with the gas phase. The invention will be further explained with reference to the following examples and comparative experiments:

COMPARATIVE EXPERIMENT A

A urea reactor in a urea plant according to the Stamicarbon $CO_2$-stripping process (see European Chemical News Urea Supplement; Jan. 17, 1969; pp. 117–20) has 10 perforated trays as partially shown in FIG. 1. The urea reactor operates at a pressure of 14.8 MPa and the temperature at the top of the reactor is 187° C. Under these conditions the degree of conversion of $CO_2$ to urea in the liquid mixture that leaves the reactor is 61.7 mole %; the degree of conversion of $NH_3$ to urea in this liquid mixture is 39.2 mole %. The high-pressure steam consumption in the high-pressure $CO_2$ stripper placed after the reactor is 862 kg of steam per ton of urea produced. This high-pressure steam is used to separate the non-converted ammonia and carbon dioxide from the urea/water mixture.

EXAMPLE 1

In the same urea plant as described in Comparative Experiment A the 10 perforated reactor trays were modified as indicated in FIG. 2. Each compartment, formed between two reactor trays, has a cylinder. The urea reactor again operates at a pressure of 14.8 MPa and the temperature at the top of the reactor is likewise 187° C. Under these comparable conditions the degree of conversion of $CO_2$ to urea is greater than 63 mole % and the degree of conversion of $NH_3$ to urea is greater than 40 mole %. The amount of steam consumed by the $CO_2$ stripper placed after the reactor is less than 800 kg per ton of urea produced while the same degree of ammonia and carbon dioxide dissociation has taken place in this stripper as in Comparative Experiment A.

COMPARATIVE EXPERIMENT B

A hydrolyzer in which urea is hydrolyzed with the aid of high-pressure steam to form ammonia and carbon dioxide was fitted with a number of horizontally placed perforated trays as shown in FIG. 3. The hydrolyzer operates at a pressure of 1.9 MPa and high-pressure steam is fed to this hydrolyser. The temperature at the top of the hydrolyser is 200° C. while the temperature at the bottom of the hydrolyzer is 210° C. An aqueous solution containing 1.2 wt. % urea is fed to the top of the hydrolyzer. The aqueous mixture that leaves the hydrolyzer via the bottom contains 5 ppm urea.

EXAMPLE 2

In the same hydrolyzer as described in Experiment B the perforated hydrolyzer trays were modified as indicated in FIG. 4. Each compartment, formed between two adjacent hydrolyzer trays, has a cylinder. The hydrolyzer again operates at a pressure of 1.9 MPa and the same amount of steam as in Comparative Experiment B is supplied to this hydrolyser, too. The temperature at the top is 200° C. and the temperature at the bottom is 210° C. The same aqueous solution, containing 1.2 wt. % urea, was fed to the top of the hydrolyzer as in Comparative Example B. The aqueous mixture that left the bottom of the hydrolyser contained less than 1 ppm urea.

What is claimed is:

1. A reactor for preparing urea from ammonia and carbon dioxide comprising a reactor shell defining a reactor wall, a cylinder, and two perforated trays, an upper tray and a lower tray, the separation between the trays defining a tray spacing distance, wherein the trays are configured to provide a gas transport path through the reactor, the gas transport path comprising a plurality of perforations in each tray, the perforations being arranged in a central portion of the tray and surrounded by an outer unperforated portion of the tray, the outermost extension of the unperforated portion defining a tray edge;

the trays are further configured to provide a liquid transport path through the reactor, the liquid transport path comprising at least one opening for each tray selected from a group consisting of an opening formed in the tray, the opening being substantially larger than the perforations and located in the outer unperforated portion of the tray, and an opening formed between the tray edge and the inside of the reactor wall, the upper tray further including a downwardly extending flange formed on the underside of the tray and outwardly of the perforations, for maintaining a gas cushion under the tray, and the lower tray further including an upwardly extending rim formed on the top side of the tray and surrounding the perforations in the tray and the cylinder positioned between the upper tray and the lower tray, wherein the diameter of the cylinder is both smaller than the downwardly extending flange of the upper tray and larger than the upwardly extending rim on the top side of the lower tray, and further wherein the height of the cylinder is 40–80% of the tray spacing distance.

2. A reactor according to claim 1 wherein each of the trays is substantially circular and have substantially the same diameter and wherein the downwardly extending flange and the upwardly extending rim are both substantially cylindrical.

3. A reactor according to claim 2 wherein the open cylinder is substantially centered, both vertically and horizontally, between the upper and lower trays.

4. A reactor according to claim 2, wherein the height of the downwardly extending flange is between 5% and 50% of the tray spacing distance.

5. A reactor according to claim 2 wherein the height of the upwardly extending rim is between 5% and 50% of the tray spacing distance.

6. A reactor according to claim 2, 4, or 5 wherein the diameter of the cylinder is between 40% and 80% of the diameter of the upper and lower trays.

7. A reactor according to claim 2 further comprising at least five perforated trays arranged in a vertically aligned configuration wherein the tray spacing distance between each pair of adjacent trays is substantially uniform.

8. A reactor according to claim 2 wherein the perforated trays are provided with an opening in the unperforated portion of the tray, wherein the opening is positioned outwardly from both the upwardly facing rim and the downwardly facing flange.

9. A reactor for manufacturing urea from a two phase gas/liquid mixture comprising ammonia, carbon dioxide, water, and ammnonium carbarnate, the reactor comprising a reactor shell defining a reactor wall, and a plurality of substantially identical compartments, each compartment comprising a cylinder, and two perforated trays, an upper tray and a lower tray, the separation between the trays defining a tray spacing distance, wherein the trays are configured to provide a gas transport path through the reactor, the gas transport path comprising a plurality of perforations in each tray, the perforations being arranged in a central portion of each tray and surrounded by an outer unperforated portion of the tray;

the trays are further configured to provide a liquid transport path through the reactor, the liquid transport path extending through a plurality of openings located outwardly from the central portion of the trays, each of the upper trays further including a downwardly extending flange, formed outwardly from the perforations and defining a flange perimeter, for maintaining a gas cushion under the tray, and each of the lower trays further including an upwardly extending rim formed inwardly from the edge and defining a rim perimeter, the upwardly extending rim surrounding the perforations in the lower tray, and a cylinder, positioned substantially vertically between adjacent trays and defining an upper opening, a lower opening, and a cylinder sidewall, the cylinder sidewall in combination with the reactor sidewall defining a substantially annular space, wherein the upper opening is within the flange perimeter of the upper tray, and wherein the lower opening surrounds the rim perimeter of the lower tray, and further wherein the height of the cylinder 40–80% of the tray spacing distance, the movement of the two phase gas/liquid mixture upwardly through the cylinder causing the liquid present in the annular space between the cylinder sidewall and the reactor sidewall to be drawn into the cylinder through the lower opening, flow upwardly through the cylinder, and be expelled through the upper opening.

10. A reactor according to claim 9 wherein the cylinder is substantially centered, both vertically and horizontally, between adjacent trays.

11. A reactor according to claim 9, wherein the height of the downwardly extending flange is between 5% and 50% of the tray spacing distance.

12. A reactor according to claim 9 wherein the height of the upwardly extending rim is between 5% and 50% of the tray spacing distance.

13. A reactor according to claim 9, 11, or 12 wherein the diameter of the cylinder is between 40% and 80% of the diameter of the tray.

14. A reactor according to claim 9 wherein the height of the downwardly extending flange is between 5% and 50% of the tray spacing distance and the height of the upwardly extending rim is between 5% and 50% of the tray spacing distance.

* * * * *